United States Patent
Gross

(10) Patent No.: US 7,189,406 B1
(45) Date of Patent: Mar. 13, 2007

(54) COMPOSITION AND METHOD FOR TREATING SKIN

(76) Inventor: Dennis Gross, 1185 Park Ave., New York, NY (US) 10128

( * ) Notice: Subject to any disclaimer, the term of this patent is extended or adjusted under 35 U.S.C. 154(b) by 319 days.

(21) Appl. No.: 09/338,729

(22) Filed: Jun. 23, 1999

(51) Int. Cl.
*A61K 8/36* (2006.01)
*A61K 8/365* (2006.01)

(52) U.S. Cl. ............ 424/401; 514/159; 514/163; 514/845; 514/847

(58) Field of Classification Search ........ 424/401, 424/443, 70.1, 70.31, 78.03; 514/844, 846
See application file for complete search history.

(56) References Cited

U.S. PATENT DOCUMENTS

| | | | |
|---|---|---|---|
| 4,797,273 A * | 1/1989 | Linn et al. ............. | 424/59 |
| 5,242,433 A * | 9/1993 | Smith et al. ........... | 604/289 |
| 5,304,370 A * | 4/1994 | Hawkins et al. ........ | 424/71 |
| 5,505,948 A * | 4/1996 | Rapaport ............... | 424/401 |
| 5,612,324 A | 3/1997 | Guang Lin et al. ..... | 514/162 |
| 5,616,332 A | 4/1997 | Herstein ............... | 424/401 |
| 5,620,694 A | 4/1997 | Girardot ............... | 424/402 |
| 5,710,141 A | 1/1998 | Lin et al. .............. | 514/162 |
| 5,720,949 A * | 2/1998 | Davis | |
| 5,730,991 A | 3/1998 | Rapaport ............... | 424/401 |
| 5,744,149 A | 4/1998 | Girardot ............... | 424/402 |
| 5,804,203 A * | 9/1998 | Hahn et al. ........... | 424/401 |
| 5,811,111 A * | 9/1998 | McAtee et al. ......... | 424/401 |
| 5,914,116 A | 6/1999 | Suares et al. | |
| 6,171,347 B1 * | 1/2001 | Kunz et al. ............ | 8/407 |
| 6,531,116 B1 | 3/2003 | Suares et al. | |
| 2002/0098210 A1 * | 7/2002 | Hahn et al. ........... | 424/401 |

FOREIGN PATENT DOCUMENTS

WO  WO-98/22078 A1 *  5/1998

OTHER PUBLICATIONS

Hawley, Gessner G., The Condensed Chemical Dictionary, 10th Ed., Van Nostrand Reinhold Co., New York, 1981, p. 838.*
Database REGISTRY on STN, RN:9005-64-5, Polysorbate-20.*

* cited by examiner

*Primary Examiner*—Sreeni Padmanabhan
*Assistant Examiner*—Gina C. Yu
(74) *Attorney, Agent, or Firm*—Kenyon & Kenyon LLP

(57) ABSTRACT

A two-step method for the topical treatment of skin aging and acne and the improvement of skin appearance is disclosed. Compositions for use in this method and a kit containing such compositions are also disclosed. The compositions and methods are effective but gentle enough suitable for daily home use by the consumer.

53 Claims, No Drawings

COMPOSITION AND METHOD FOR TREATING SKIN

FIELD OF THE INVENTION

The present invention relates to dermatological compositions and methods, and more particularly to compositions and methods for use by consumers for the topical treatment of skin aging, acne, etc. and for the improvement of skin appearance.

BACKGROUND OF THE INVENTION

Skin renewal can be stimulated by removal of the outer keratinous layer of the skin system. Such removal can be effected mechanically, for example, by rubbing with an abrasive composition, or chemically. Chemical exfoliation and peeling are effected by agents that interact with the complex structure of the skin, removing the outer layer to expose the underlying layers. Skin-renewal stimulating compositions and agents can provide anti-aging benefits, for example, a reduction of keratoses, freckles, wrinkles, fine lines and epidermal and dermal atrophy. The newly exposed skin is smoother and appears younger.

In recent years the use of cosmetic and pharmacological formulations containing skin-renewal simulating acids, such as alpha hydroxy acids ("AHAs") or retinoic acid, to obtain antiaging and dermatologically therapeutic benefits has become widespread. Scientific and clinical reports, as well as much subjective evidence, have shown that substantial improvements in skin appearance and condition can be obtained by means of skin-renewal stimulating acids, which are believed to be attributable to increased rates of skin cell renewal, and the removal of outer layers of dead cells. But it is also well known that skin-renewal stimulating acids can be irritating, and that the irritation they induce is often a long-term effect manifested several weeks after use of the acids. In extreme cases the irritation can be severe and painful.

Skin renewal stimulating acids are also effective for treating acne, a common inflammatory pilosebaceous disease characterized by comedones, papules, pustules, and superficial pus-filled cysts. The earliest symptom of acne is hyperkeratosis of the upper part of the pilosebaceous follicle, which leads to obstruction of the pilosebaceous follicle with consequent formation of the comedone composed of sebum, keratin and microorganisms, particularly *Propionibacterium (Corynebacterium) acnes*. Lipases from *P. acnes* break down triglycerides in the sebum to form free fatty acids, which irritate the follicular wall. Retention of sebaceous secretions and dilation of the follicle may lead to cyst formation. Rupture of the follicle with release of the contents into the tissues induces an inflammatory reaction that may heal with scarring.

Salicylic acid is a well recognized anti-acne ingredient that causes a reduction in intercellular cohesion of the corneocytes. It is believed that salicylic acid also works by dissolving existing keratin plugs as well as preventing the formation of new ones. But compliance by users with a regimen of treatment involving repeated application of salicylic acid products is often less than ideal, because, like AHAs, salicylic acid tends to be somewhat drying and irritating and can often cause peeling, causing individuals to use the products less frequently and copiously than is necessary to obtain an optimum benefit As noted in U.S. Pat. No. 5,505,948 to Rapport, in the prior art, peeling of the skin using acids has been done in dermatologists', aestheticians' and cosmetologists' offices, and has been accomplished in a period of minutes or hours, generally in a single visit. Such chemical peels use relatively high concentrations of such peeling agents as glycolic acid, trichloroacetic acid and phenol compounded into a suitable vehicle, with concentrations being typically from 30% up to as much as 90%, and thus are quick, harsh, and often painful. In the past, where the peeling compositions have been left on the skin under the direction of a doctor or other professional, the effect of a relatively long duration of skin contact with the peeling compositions has been wounding and irritation of the skin due to the high concentrations of the peeling agents.

Chemical peeling can be done in varying degrees of depth. A light or superficial peel is generally one which is comparatively superficial in effect, and medium or deep chemical peels are ones in which peeling agents are used to produce a moderate to severe wound to the skin. Medium or deep peels achieve a much more dramatic and visible effect, and do so quickly, in minutes or hours, but usually result in pain and inflammation of the skin. Because of the strength and attendant risks of such peels, prior art peels capable of producing significant and visible effects have been limited to use by professionals such as doctors, cosmetologists and aestheticians.

Previously, in order to be safe enough for home use, the acid concentration had to be so low that the visible, dramatic results of medium or deep peel could not be achieved by the consumer at home. It has now been surprisingly found, however, that visible, dramatic results can be obtained from a two step process safe enough for use by the consumer at home, as often as once a day.

In view of the foregoing limitations and shortcomings of the prior art compositions and methods, as well as other disadvantages not specifically mentioned above, it should be apparent that there still exists a need in the art for a product that is effective for the topical treatment of skin aging, acne etc. and for the improvement of skin appearance that is safe enough for use at home by the consumer.

SUMMARY OF THE INVENTION

The present invention is directed to a two-step acid peel for the skin gentle enough for use by the consumer at home but capable of providing an improvement in the skin comparable to results previously obtainable only by professionals using higher concentrations of acid. This method comprises the steps of applying to the skin a first composition comprising a skin renewing acid component in a cosmetically acceptable vehicle, wherein the pH of the first composition is between about 2.5 and about 4, and neutralizing the first composition by applying to the skin a second composition comprising an alkaline agent and from about 0.1 to about 10% of at least one surfactant/emulsifying agent in a cosmetically acceptable vehicle, wherein the pH of the second composition is greater than about 7.

The present invention is also directed to compositions for the neutralization of an acid peel comprising an alkaline agent and about 0.1 to about 10 percent of at least one surfactant/emulsifying agent, wherein the pH of the composition is greater than about 7.

The present invention is further directed to a kit for use by the consumer to perform an acid skin peel at home comprising a first composition comprising a skin renewing acid in a cosmetically acceptable vehicle, the first composition having a pH between about 2.5 and about 4, a second composition comprising an alkaline agent and about 0.1 to about 10 percent of at least one surfactant/emulsifying agent in a cosmetically acceptable vehicle, the second composition having a pH greater than about 7, and a means for applying the first and second compositions sequentially to the skin.

With the foregoing and other objects, advantages and features of the invention that will become hereinafter apparent, the nature of the invention may be more clearly understood by reference to the following detailed description of the invention and the appended claims.

DETAILED DESCRIPTION OF THE INVENTION

All percentages and ratios used herein are by weight of the total composition and all measurements made at 25° C., unless otherwise designated. All percentages are on a weight/weight basis.

As used herein the term "dermatological composition" means a composition useful for topical application to the skin of a human.

As used herein, the term "topical application" means to apply or spread the compositions of the present invention to the surface of the skin.

As used herein, the term "cosmetically acceptable" means that the compositions or components thereof so described are of sufficiently high purity and suitable for use in contact with human skin without undue toxicity, incompatibility, instability, allergic response, and the like.

One preferred method of application is via single-use pads containing a calibrated amount of the compositions of the present invention. Pads are disposable, convenient and sanitary. Pads suitable for use in the current invention may be made of woven or nonwoven cloth, paper, sponges. Natural or synthetic fibers may be used. Preferred pads are made of cotton or a cotton/synthetic blend. They may comprise a single layer, or multiple layers. The use of pads presaturated with the compositions of the present invention is convenient for the user and allows for consistency from one treatment to the next.

Other preferred methods of application include cotton balls and cotton-tipped applicators moistened with the compositions of the present invention.

Step One: Acid Pad

The skin-renewal stimulating acid can be a hydrophilic acid or other acid-equivalent electronegatively hydrophilic organic compound selected from the group consisting of hydroxy carboxylic acids, keto acids, hydroxybenzoic acids and related compounds. Preferred compounds have a relatively lower molecular weight as higher molecular weight compounds tend to be hydrophobic and may have too little activity. Since the smallest molecules such as formic acid, are unduly aggressive, a preferred molecular weight range is from about 50 to about 250.

Preferred acids include alpha-hydroxy acids, salicylic acid and other beta hydroxy acids, and combination thereof. Preferably the composition of Step 1 includes at least one alpha hydroxy acid selected from the group consisting of glycolic acid, lactic acid, malic acid, tartaric acid, citric acid and ascorbic acid. Other preferred skin-renewal stimulating acids include mandelic acid, azelaic acid, glyceric acid, tartronic acid, gluconic acid, benzylic acid, pyruvic acid, ethyl pyruvate, 2-hydroxybutyric acid, salicylic acid, and mixtures thereof. Mineral acids in appropriate concentrations also may stimulate skin cell renewal as well as non-hydroxy acids, for example trichloracetic acid.

Various skin-renewal stimulating acids may be combined together, and simple tests can be used to evaluate their efficacy and side effects, for incorporation into cosmetics suitable for application to the skin.

Preferred are acids with good, cosmetically acceptable characteristics, especially freedom from any unpleasant odor, low or substantially no toxicity, stability for shelf life, freedom from regulatory problems, known and tolerable side effects and a white or colorless appearance in the end product composition.

Salicylic acid, also known as 2-hydroxybenzoic acid, is a white crystalline powder having a melting point from about 157° to 159° C. See *The Merck Index*, Twelfth Edition, entry 8484, p. 1433 (1996), incorporated herein by reference. The salicylic acid of the compositions useful herein is present from about 0.1% to about 5%, preferably from about 1% to about 3%, and most preferably it comprises about 2%.

It has been surprisingly found that the addition of a surfactant/emulsifying agent to the low pH carrier significantly improves the performance of the composition, allowing the use of significantly lower concentrations of acid to achieve the same result. One or more surfactant/emulsifying agents can be used; all surfactant/emulsifying agents present in the composition of step 1 combined comprise from about 0.1% to about 10%. Preferably the surfactants comprise from about 2% to about 6%. Most preferably the surfactants comprise from about 3% to about 5%. Surfactants suitable for use in the present invention include cetearaths, ceteths, cetyl alcohol, deceths, dodoxynols, glyceryl palmitate, glyceryl stearate, laneths, myreths, nonoxynols, octoxynols, oleths, PEG-castor oil, poloxamers, poloxamines, polysorbates, ammonium laureth sulfate and sodium laureth sulfate. Other suitable surfactant/emulsifying agents would be known to one of skill in the art and are listed in the *CTFA International Cosmetic Ingredient Dictionary and Handbook*, Vol. 2, 7th Edition (1997). Preferred surfactants include octoxynol-9 and polysorbate-20.

The pH of the formulation is an important factor in the availability of the acid and the stability of the formulation of step 1 of the claimed invention. A low pH is necessary in order to suppress ionization and enhance the penetration of the acid into the stratum corneum. Preferably the pH range for the first pad is between about 2.5 and about 4. More preferably the pH range is between about 3 and about 4.

A wide variety of acids, bases, and buffers can be utilized to adjust and/or maintain the pH of the compositions useful in the present invention. Examples of materials useful for adjusting and/or maintaining the pH include, without limitation, ammonia, sodium carbonate, sodium hydroxide, triethanolamine, hydrochloric acid, phosphoric acid, sodium hydrogen phosphate, sodium dihydrogen phosphate, citric acid, and the like.

These ingredients are present in a safe and effective amount in a topical cosmetically acceptable carrier, which can be of a variety of different forms. By "safe and effective" is meant an amount sufficient to act as a suitable vehicle for the required components and any other optional components, but not so much as to cause any side effects or skin reactions. The typical carrier can be in the form of an aqueous or hydro alcoholic system, or an emulsion system. The emulsions can also include microemulsion systems.

The pharmaceutically-acceptable topical carrier, in total, typically comprises from about 0.1% to about 95% by weight of the composition of step one of the present invention, preferably from about 70% to about 91%, and most preferably from about 80% to about 90%.

A particularly preferred carrier for use in the presently claimed compositions and method is a hydro alcoholic system comprising from about 1% to about 99% ethanol, isopropanol or mixtures thereof, and from about 1% to about 99% water. Preferred carriers comprise from about 1% to about 50% ethanol, isopropanol, or mixtures thereof, and from about 50% to about 99% water. Most preferred carriers comprise from about 5% to about 10% of ethanol, isopropanol, or mixtures thereof, and from about 90% to about 95% water.

The compositions of the present invention can comprise a wide range of additional components. Such components include, without limitation, absorbents, antifoaming agents, antimicrobial agents, antioxidants, binders, biological additives, chelating agents (e.g. disodium EDTA, tetrasodium EDTA, sodium metasilicate, etc.), denaturants, external analgesics (e.g. aspirin, nonsteroidal antiinflammatories), steroidal antiinflammatory drugs (such as hydrocortisone and the like), preservatives (e.g. imidazolidinyl urea, diazolidinyl urea, phenoxyethanol, methylparaben, ethylparaben, propylparaben, etc.), reducing agents, skin bleaching agents (e.g. hydroquinone, kojic acid, sodium metabisulfite, etc.), skin protectants, solubilizing agents, solvents, and thickening agents.

Vitamins and derivatives thereof may also be added. Suitable vitamins and derivatives include Vitamin A, retinyl acetate, retinyl palmitate, Vitamin C, ascorbic acid, ascorbyl palmitate, magnesium ascorbyl palmitate, magnesium ascorbyl phosphate, Vitamin E, and tocopherol.

A preferred optional component is at least one skin conditioning agent. Skin conditioning agents include emollients, humectants and moisturizers. A variety of these materials can be employed and each can be present at a level of from about 0.1% to about 50%, more preferably from about 1% to about 10% and most preferably from about 1% to about 5%. These materials include urea; guanidine; aloe vera; polyhydroxy alcohols such as sorbitol, glycerol, hexanetriol, propylene glycol, hexylene glycol and the like; polyethylene glycol; sugars, starches and derivatives thereof; hyaluronic acid, and the like. Preferred skin conditioning agents include volatile and nonvolatile silicone oils.

Anti-acne agents may also be included. Such anti-acne ingredients include, without limitation, sulfur, resorcinol, pyruvic acid, retinoids such as retinoic acid and its derivatives, and antimicrobials (such as benzoyl peroxide, erythromycin, tetracycline, triclosan, azelaic acid, clindamycin, chlorhexidine, tetracycline, neomycin, miconazole, clotrimazole and the like).

Aesthetic components such as fragrances, pigments, colorants, essential oils, skin sensates, astringents, skin soothing agents, skin healing agents and the like may also be included. Suitable aesthetic components include clove oil, menthol, camphor, eucalyptus oil, eugenol, menthyl lactate, witch hazel distillate, bisabolol, and the like. Witch hazel distillate, green tea extract and menthyl lactate are preferred aesthetic components.

Step 2: Neutralizer Pad

The second step of the method of the claimed invention comprises application of a composition containing an alkaline agent and having a pH high enough to neutralize the composition of Step 1 after it has been applied to the skin. Preferably sodium bicarbonate is used to adjust the pH to an appropriate level, i.e. greater than 7. Sodium hydroxide or other alkaline agents may be used to adjust the pH in place of sodium bicarbonate.

It has been surprisingly found that the addition of a surfactant/emulsifying agent to the high pH composition of Step 2 significantly improves the performance of the composition. By decreasing the droplet size and decreasing the surface tension of the composition, the surfactant/emulsifying agent increases penetration and delivery, and potentiates its effects, allowing a less alkaline pH to be used in Step 2 (and a more acidic pH in Step 1), while mitigating adverse effects and making sure all of the acid is neutralized. The resulting composition is thus gentle enough for home use by the consumer as frequently as once a day and overcomes the problems described in U.S. Pat. No. 5,505,948 to Rappaport, while still producing a significant improvement in the appearance of the skin comparable to the improvements that previously could only be achieved with the use of higher percentages of acid by doctors and other professionals. One or more surfactant/emulsifying agents can be used; all surfactant/emulsifying agents present combined comprise from about 0.1% to about 10%. Preferably the surfactant/emulsifying agents comprise from about 1% to about 5%. Most preferably they comprise from about 2% to about 3%. Surfactant/emulsifying agents suitable for use in the composition of step 2 include those listed above for the composition of step 1. Preferred surfactant/emulsifying agents include octoxynol-9 and polysorbate-20. Other suitable surfactant/emulsifying agents include those listed above as suitable for use in the composition of Step 1.

The pH of the formulation is an important factor in the ability of the formulation to safely neutralize the formulation of Step 1. A high pH is necessary because it is believed that the rapid fluctuation in pH is responsible for many of the benefits of the claimed invention over the prior art, allowing beneficial effects to occur without the need for harsh peeling of the outer layers of the skin, as taught by the prior art. Preferably the pH of the second pad is between about 7.1 and about 12. More preferably it is between about 8 and about 8.5. Preferably there is approximately a change of 4 in pH between the first step and the second step.

These ingredients are present in a safe and effective amount in a topical cosmetically acceptable carrier, which can be of a variety of different forms. By "safe and effective" is meant an amount sufficient to act as a suitable vehicle for the required components and any other optional components, but not so much as to cause any side effects or skin reactions. In other words, these carriers are suitable for use on human skin. The typical carrier can be in the form of an aqueous system, a hydro alcoholic system, an anhydrous oil or silicone based system, or an emulsion system.

The compositions of Step 2 of the present invention can comprise a wide range of additional components, including those listed above for the compositions of Step 1.

Vitamins and derivatives thereof, including those listed above for the composition of Step 1, may also be added.

A preferred optional component is at least one skin conditioning agent. Skin conditioning agents include emollients, humectants and moisturizers. A variety of these materials can be employed and each can be present at a level of from about 0.1% to abut 20%, more preferably from about 1% to about 10% and most preferably from about 2% to about 5%. Preferred skin conditioning agents include and volatile and nonvolatile silicone oils. Silicones such as polydialkylsiloxanes, polydiarylsiloxanes, polyalkarylsiloxanes and cyclomethicones having 3 to 9 silicon atoms are useful oils.

Aesthetic components such as fragrances, pigments, colorants, essential oils, astringents, skin soothing agents, skin healing agents and the like may also be included. A preferred aesthetic component is green tea extract.

Method of Use

The present invention also relates to a method for treating skin aging and acne in mammalian skin, and improving the skin's appearance. Such a method comprises topically applying to the skin a pad or other means for delivering an effective amount of a composition containing an effective amount of an acne-composition. The term "effective amount," as used herein, means an amount sufficient to provide an anti-acne benefit. Typically, an effective coating of the skin is from about 0.01 mg salicylic acid or composition of the present invention/cm$^2$ skin to about 5 mg/cm$^2$. The method of the present invention does not require degreasing of the skin prior to application of the first pad.

The method should be practiced at least as often as once a month and may be practiced as often as once a day. A preferred method of treating the skin is via chronic topical application. By "chronic" application, it is meant herein that the period of topical application may be over the lifetime of the subject.

Preferably the skin is washed prior to application of the first step of the peel. The formulation of step 1 is applied all over the area of the skin to be treated, preferably in a circular motion, and allowed to dry for approximately 3 minutes. The formulation of step 2 is then applied in the same manner and allowed to dry completely. After step 2 is dried, moisturizer, sunscreen and/or makeup may be applied as usual. Neither formulation should be rinsed off of the skin.

As a result of the rapid change in pH when the composition of Step 1 is neutralized by the composition of Step 2, there is an increase in vasopermeability causing slight edema in the skin, which helps reduce the appearance of lines and gives the skin a healthy appearance. This may be caused by the warmth generated by the exothermic reaction that occurs when the composition of Step 2 reacts with the composition of Step 1 on the skin. The neutralization step potentiates the anti-aging and anti-acne effects of the acid step, which are further potentiated by the ability of the consumer to use the present invention as often as once a day, and by the conversion of the acid(s) to their salt forms, which are also dermatologically active.

The compositions of the claimed invention are useful in reducing fine wrinkles and lines, reducing pore size, exfoliating the skin, eliminating acne, toning the skin, enhancing the skin's radiancy, and providing softer, smoother skin with a more uniform appearance.

The present invention also includes a kit containing the acid-containing composition of step 1, the neutralizer composition of step 2, and a means for applying the compositions to the skin. Preferably the compositions of step 1 and step 2 are provided on a series of single-use pads, half pre-saturated with a calibrated amount of the composition of step 1 and the other half pre-saturated with a calibrated amount of the composition of step 2.

EXAMPLES

The invention will be more fully described and understood with reference to the following examples, which are given by way of illustration and are not intended to limit the scope of the invention in any way.

Example 1

Acid Pad

The following table provides ranges for representative ingredients for formulating the acid pad for use in Step 1 of the claimed method.

| Ingredient | Weight Percent | |
|---|---|---|
| | From About | To About |
| Chelating agent | 0.01% | 0.3% |
| Witch Hazel Distillate | 0.01% | 20.0% |
| Surfactant/Emulsifying Agent | 0.01% | 25.0% |
| Salicylic Acid | 0.1% | 5.0% |
| Lactic Acid | 0.1% | 20.0% |
| Glycolic Acid | 0.1% | 20.0% |
| Ammonia, dissolved | 0.0% | 35.0% |
| Preservative | 0.01% | 2.0% |
| Acetone | 0.0% | 10.0% |
| Alcohol | 1.0% | 50.0% |
| Purified Water | | q.s. 100.0% |

Example 2

Acid Pad

The following ingredients are combined in the proportions indicated.

| Ingredient | Weight Percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid USP | 2.0% |
| Lactic Acid USP | 2.0% |
| Glycolic Acid | 15.0% |
| Ammonia, dissolved | 6.0% |
| Imidazolidinyl Urea | 0.2% |
| Acetone | 5.0% |
| Ethanol | 5.0% |
| Purified Water | q.s. 100.0% |

Cotton pads are then saturated with approximately 0.05–0.2 cc/pad of this composition.

Example 3

Acid Pad

The following ingredients are combined in the proportions indicated.

| Ingredient | Weight Percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid USP | 2.0% |
| Lactic Acid USP | 2.0% |
| Glycolic Acid | 15.0% |

-continued

| Ingredient | Weight Percent |
| --- | --- |
| Resorcinol | 2.0% |
| Ammonia, dissolved | 6.0% |
| Imidazolidinyl Urea | 0.2% |
| Isopropanol | 5.0% |
| Purified Water | q.s. 100.0% |

Cotton pads are then saturated with approximately 0.05–0.2 cc/pad of this composition.

Example 4

Neutralizer Pad

The following table provides ranges for representative ingredients for formulating the neutralizer pad for use in Step 2 of the claimed method.

| | Weight Percent | |
| --- | --- | --- |
| Ingredient | From About | To About |
| Sodium Bicarbonate | 0.1% | 15.0% |
| Silicone | 0.0% | 50.0% |
| Green Tea Extract | 0.0% | 75.0% |
| Phospholipids | 0.0% | 10.0% |
| Vitamin E | 0.0% | 10.0% |
| Vitamin A | 0.0% | 10.0% |
| Ascorbyl Palmitate | 0.0% | 10.0% |
| Preservative | 0.0% | 6.0% |
| Chelating Agent | 0.0% | 2.0% |
| Surfactant/Emulsifying Agent | 0.1% | 10.0% |
| Water | | q.s. 100.0% |

Example 5

Neutralizer Pad

The following ingredients are combined in the proportions indicated.

| Ingredient | Weight Percent |
| --- | --- |
| Sodium Bicarbonate | 3.0% |
| Dimethicone Copolyol | 0.75% |
| Green Tea Extract | 0.2% |
| Phospholipids | 0.5% |
| Vitamin E | 0.5% |
| Vitamin A | 0.5% |
| Ascorbyl Palmitate | 0.5% |
| Phenoxyethanol | 0.01% |
| Methylparaben | 0.01% |
| Diazolidinyl Urea | 0.01% |
| Tetrasodium EDTA | 0.01% |
| Octoxynol-9 | 2.0% |
| Water | q.s. 100.0% |

Cotton pads are then saturated with approximately 0.05–0.2 cc/pad of this composition.

Example 6

Method of Use

Pad 1 is applied all over the face by gently putting on skin in a circular manner and allowing to dry for approximately 3 minutes. Pad 2 is applied in the same manner and allowed to dry on the face completely. Neither pad is rinsed.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A method for treating skin, comprising the sequential steps of:
   a) applying to the skin a first dermatological liquid composition comprising an effective amount of a skin renewal stimulating acid and a cosmetically acceptable vehicle, wherein the pH of the first dermatological liquid composition is between about 2.5 and about 4;
   b) neutralizing the first dermatological liquid composition by applying to the skin a second dermatological liquid composition comprising an alkaline agent suitable for use in a skin care composition, about 0.1% to about 10% by weight of at least one surfactant/emulsifying agent and a cosmetically acceptable vehicle, wherein the pH of the second dermatological liquid composition ranges from greater than about 7 to about 12;
   c) allowing the second dermatological liquid compositions to dry on the skin; and
   d) applying to the skin a moisturizer, sun screen and/or makeup when the first and second dermatological liquid compositions remain on the skin.

2. The method of claim 1 wherein the pH of the second dermatological liquid composition is between about 7.1 and about 12.

3. The method of claim 2 wherein the pH of the second dermatological liquid composition is between about 8 and about 8.5.

4. The method of claim 1 wherein the amount of the at least one surfactant/emulsifying agent in the second dermatological liquid composition is from about 1% to about 5%.

5. The method of claim 4 wherein the amount of the at least one surfactant/emulsifying agent in the second dermatological liquid composition is from about 2% to about 3%.

6. The method of claim 5 wherein the at least one surfactant/emulsifying agent of the second dermatological liquid composition is selected from the group consisting of cetearaths, ceteths, cetyl alcohol, deceths, dodoxynols, glyceryl palmitate, glyceryl stearate, laneths, myreths, nonoxynols, octoxynols, oleths, PEG-castor oil, poloxamers, poloxamines, polysorbates, ammonium laureth sulfate, sodium laureth sulfate, and mixtures thereof.

7. The method of claim 1 wherein the acid in the first dermatological liquid composition is present from about 1% to about 3%.

8. The method of claim 7 wherein the acid in the first dermatological liquid composition is present in about 2%.

9. The method of claim 1 wherein the first dermatological liquid composition and the second dermatological liquid composition are each applied with use of a pad.

10. The method of claim 1 wherein the first dermatological liquid composition and the second dermatological liquid composition are each applied with use of a cotton ball.

11. The method of claim 1 wherein the first dermatological liquid composition and the second dermatological liquid composition are each applied with use of a cotton-tipped applicator.

12. The method of claim 1 wherein the effective amount of the acid is from about 0.1% to about 5%.

13. The method of claim 1 wherein the acid is a hydrophilic acid.

14. The method of claim 1 wherein the first dermatological liquid composition and the second dermatological liquid composition are applied to a face.

15. The method of claim 1 wherein the first dermatological liquid composition is allowed to dry on the skin for about 3 minutes.

16. The method of claim 1, wherein the acid in the first dermatological liquid composition is selected from the group consisting of hydroxy carboxylic acids, keto acids, hydroxybenzoic acids and mixtures thereof.

17. The method of claim 16, wherein the acid in the first dermatological liquid composition is selected from alpha hydroxy acids and mixtures thereof.

18. The method of claim 16, wherein the acid in the first dermatological liquid composition is selected from the group consisting of glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, and mixtures thereof.

19. The method of claim 1, wherein the first dermatological liquid composition further comprises at least one surfactant/emulsifying agent.

20. The method of claim 1, wherein the first dermatological liquid composition further comprises about 0.1% to about 10% by weight of at least one surfactant/emulsifying agent.

21. The method of claim 1, wherein the first dermatological liquid composition further comprises about 2% to about 6% by weight of at least one surfactant/emulsifying agent.

22. The method of claim 1, wherein the first dermatological liquid composition further comprises about 3% to about 5% by weight of at least one surfactant/emulsifying agent.

23. The method of claim 19, wherein the at least one surfactant/emulsifying agent in the first dermatological liquid composition is selected from the group consisting of ceteareths, ceteths, cetyl alcohol, deceths, dodoxynols, glyceryl palmitate, glyceryl stearate, laneths, myreths, nonoxynols, octoxynols, oleths, PEG-castor oil, poloxamers, poloxamines, polysorbates, ammonium laureth sulfate, sodium laureth sulfate, and mixtures thereof.

24. The method of claim 23, wherein the at least one surfactant/emulsifying agent in the first dermatological liquid composition is selected from the group consisting of octoxynol-9 and polysorbate-20.

25. The method of claim 6, wherein the at least one surfactant/emulsifying agent in the second dermatological liquid composition is selected from the group consisting of octoxynol-9 and polysorbate-20.

26. The method of claim 1, wherein the alkaline agent in the second dermatological liquid composition is selected from sodium bicarbonate, sodium carbonate, sodium hydroxide, ammonia, triethanolamine, sodium hydrogen phosphate and sodium dihydrogen phosphate.

27. The method of claim 26, wherein the alkaline agent in the second dermatological liquid composition is sodium bicarbonate or sodium carbonate.

28. The method of claim 26, wherein the alkaline agent in the second dermatological liquid composition is selected from sodium hydroxide, ammonia and triethanolamine.

29. The method of claim 1, wherein the first dermatological liquid composition is applied to the skin by massaging into the skin in step a), and the second dermatological liquid composition is applied to the skin by massaging into the skin in step b).

30. The method of claim 1, wherein the first dermatological liquid composition is applied to the skin by massaging into the skin with a pad saturated with the first dermatological liquid composition in step a), and the second dermatological liquid composition is applied to the skin by massaging into the skin with a pad saturated with the second dermatological liquid composition in step b).

31. The method of claim 1, wherein the first dermatological liquid composition is allowed to dry on the skin after step a) and before step b).

32. The method of claim 1, wherein the pH of the skin immediately after step a) is changed by approximately 4 with step b).

33. The method of claim 1, wherein the skin is the skin of a consumer.

34. The method of claim 33, wherein the skin is the skin on the face of a consumer.

35. The method of claim 1, wherein the pH of the first dermatological liquid composition is between about 3 and about 4.

36. The method of claim 26, wherein the alkaline agent in the second dermatological liquid composition is sodium bicarbonate.

37. The method of claim 1, wherein the first dermatological liquid composition comprises:

| ingredient | weight percent from | to |
| --- | --- | --- |
| chelating agent | 0.01% | 0.3% |
| witch hazel distillate | 0.01% | 20.0% |
| surfactant/emulsifying agent | 0.01% | 25.0% |
| salicylic acid | 0.1% | 5.0% |
| lactic acid | 0.1% | 20.0% |
| glycolic acid | 0.1% | 20.0% |
| ammonia, dissolved | 0.0% | 35.0% |
| preservative | 0.01% | 2.0% |
| acetone | 0.0% | 10.0% |
| alcohol | 1.0% | 50.0% |
| purified water | balance to 100%. | |

38. The method of claim 1, wherein the second dermatological liquid composition comprises:

| ingredient | weight percent from | to |
| --- | --- | --- |
| sodium bicarbonate | 0.1% | 15.0% |
| silicone | 0.0% | 50.0% |
| green tea extract | 0.0% | 75.0% |
| phospholipids | 0.0% | 10.0% |
| vitamin E | 0.0% | 10.0% |
| vitamin A | 0.0% | 10.0% |
| ascorbyl palmitate | 0.0% | 10.0% |

-continued

| ingredient | weight percent | |
|---|---|---|
| | from | to |
| preservative | 0.0% | 6.0% |
| chelating agent | 0.0% | 2.0% |
| surfactant/emulsifying agent | 0.1% | 10.0% |
| water | balance to 100%. | |

39. The method of claim 37, wherein the second dermatological liquid composition comprises:

| ingredient | weight percent | |
|---|---|---|
| | from | to |
| sodium bicarbonate | 0.1% | 15.0% |
| silicone | 0.0% | 50.0% |
| green tea extract | 0.0% | 75.0% |
| phospholipids | 0.0% | 10.0% |
| vitamin E | 0.0% | 10.0% |
| vitamin A | 0.0% | 10.0% |
| ascorbyl palmitate | 0.0% | 10.0% |
| preservative | 0.0% | 6.0% |
| chelating agent | 0.0% | 2.0% |
| surfactant/emulsifying agent | 0.1% | 10.0% |
| water | balance to 100%. | |

40. The method of claim 1, wherein the second dermatological liquid composition comprises:

| ingredient | weight percent |
|---|---|
| sodium bicarbonate | 3.0% |
| dimethicone copolyol | 0.75% |
| green tea extract | 0.2% |
| phospholipids | 0.5% |
| vitamin E | 0.5% |
| vitamin A | 0.5% |
| ascorbyl palmitate | 0.5% |
| phenoxyethanol | 0.01% |
| methylparaben | 0.01% |
| diazolidinyl urea | 0.01% |
| tetrasodium EDTA | 0.01% |
| octoxynol-9 | 2.0% |
| water | balance to 100%. |

41. The method of claim 1, wherein the first dermatological liquid composition comprises:

| ingredient | weight percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid | 2.0% |
| Lactic Acid | 2.0% |
| Glycolic Acid | 15.0% |
| Resorcinol | 2.0% |
| Ammonia, dissolved | 6.0% |
| Imidazolidinyl Urea | 0.2% |
| Isopropanol | 5.0% |
| Water | balance to 100%; and | the second dermatological liquid composition comprises:

| ingredient | weight percent |
|---|---|
| sodium bicarbonate | 3.0% |
| dimethicone copolyol | 0.75% |
| green tea extract | 0.2% |
| phospholipids | 0.5% |
| vitamin E | 0.5% |
| vitamin A | 0.5% |
| ascorbyl palmitate | 0.5% |
| phenoxyethanol | 0.01% |
| methylparaben | 0.01% |
| diazolidinyl urea | 0.01% |
| tetrasodium EDTA | 0.01% |
| octoxynol-9 | 2.0% |
| water | balance to 100%. |

42. The method of claim 1, wherein the first dermatological liquid composition comprises:

| ingredient | weight percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid | 2.0% |
| Lactic Acid | 2.0% |
| Glycolic Acid | 15.0% |
| Ammonia, dissolved | 6.0% |
| Imidazolidinyl Urea | 0.2% |
| Acetone | 5.0% |
| Ethanol | 5.0% |
| Water | balance to 100%; and | the second dermatological liquid composition comprises:

| ingredient | weight percent |
|---|---|
| sodium bicarbonate | 3.0% |
| dimethicone copolyol | 0.75% |
| green tea extract | 0.2% |
| phospholipids | 0.5% |
| vitamin E | 0.5% |
| vitamin A | 0.5% |
| ascorbyl palmitate | 0.5% |
| phenoxyethanol | 0.01% |
| methylparaben | 0.01% |
| diazolidinyl urea | 0.01% |
| tetrasodium EDTA | 0.01% |
| octoxynol-9 | 2.0% |
| water | balance to 100%. |

43. The method of claim 1, wherein the first dermatological liquid composition comprises:

| ingredient | weight percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid | 2.0% |
| Lactic Acid | 2.0% |
| Glycolic Acid | 15.0% |
| Ammonia, dissolved | 6.0% |
| Imidazolidinyl Urea | 0.2% |

-continued

| ingredient | weight percent |
|---|---|
| Acetone | 5.0% |
| Ethanol | 5.0% |
| Purified Water | balance to 100%. |

44. The method of claim 1, wherein the first dermatological liquid composition comprises:

| ingredient | weight percent |
|---|---|
| Disodium EDTA | 0.1% |
| Sodium Benzoate | 0.2% |
| Witch Hazel Distillate | 2.5% |
| Polysorbate-20 | 1.0% |
| Salicylic Acid | 2.0% |
| Lactic Acid | 2.0% |
| Glycolic Acid | 15.0% |
| Resorcinol | 2.0% |
| Ammonia, dissolved | 6.0% |
| Imidazolidinyl Urea | 0.2% |
| Isopropanol | 5.0% |
| Purified Water | balance to 100%. |

45. The method of claim 1, wherein the acid in the first dermatological liquid composition is selected from malic acid and citric acid.

46. A method for treatment of the skin of a consumer comprising the sequential steps of:
 a) applying to the skin, by massaging into the skin, an acid peel of a first dermatological liquid composition, consisting essentially of an effective amount of an acid suitable as a skin renewing acid in a cosmetically acceptable vehicle, wherein the pH of the first dermatological liquid composition is between about 2.5 and about 4;
 b) allowing the first dermatological liquid composition to dry on the skin;
 c) neutralizing said first dermatological liquid composition by applying to the skin, by massaging into the skin, a second dermatological liquid composition, consisting essentially of an alkaline agent suitable for use in a skin care composition, and from about 0.1% to about 10% of at least one surfactant/emulsifying agent in a cosmetically acceptable vehicle, wherein the pH of the second dermatological liquid composition ranges from greater than about 7 to about 12;
 d) allowing the second dermatological liquid composition to dry; and
 e) applying a moisturizer, sunscreen and/or makeup to the skin when the first and second dermatological liquid compositions remain on the skin;
 the first dermatological liquid composition consisting essentially of:

|  | weight percent | |
|---|---|---|
| ingredient | from | to |
| chelating agent | 0.01% | 0.3% |
| witch hazel distillate | 0.01% | 20.0% |
| surfactant/emulsifying agent | 0.01% | 25.0% |
| salicylic acid | 0.1% | 5.0% |
| lactic acid | 0.1% | 20.0% |
| glycolic acid | 0.1% | 20.0% |
| ammonia, dissolved | 0.0% | 35.0% |
| preservative | 0.01% | 2.0% |
| acetone | 0.0% | 10.0% |
| alcohol | 1.0% | 50.0% |
| purified water | balance to 100%; and | | the second dermatological liquid composition consisting essentially of:

|  | weight percent | |
|---|---|---|
| ingredient | from | to |
| sodium bicarbonate | 0.1% | 15.0% |
| silicone | 0.0% | 50.0% |
| green tea extract | 0.0% | 75.0% |
| phospholipids | 0.0% | 10.0% |
| vitamin E | 0.0% | 10.0% |
| vitamin A | 0.0% | 10.0% |
| ascorbyl palmitate | 0.0% | 10.0% |
| preservative | 0.0% | 6.0% |
| chelating agent | 0.0% | 2.0% |
| surfactant/emulsifying agent | 0.1% | 10.0% |
| water | balance to 100%. | |

47. The method of claim 46 wherein the first dermatological liquid composition and the second dermatological liquid composition are applied to a face.

48. The method of claim 46 wherein the first dermatological liquid composition is allowed to dry on the skin for about 3 minutes.

49. A method for treatment of the skin of a consumer consisting essentially of the sequential steps of:
 a) applying to the skin an acid peel of a first dermatological liquid composition by massaging into the skin with a pad saturated with the first dermatological liquid composition comprising an effective amount of an acid suitable as a skin renewing acid in a cosmetically acceptable vehicle, wherein the pH of the first dermatological liquid composition is between about 2.5 and about 4;
 b) allowing the first dermatological liquid composition to dry on the skin;
 c) neutralizing said first dermatological liquid composition by applying to the skin a second dermatological liquid composition by massaging into the skin with a pad saturated with the second dermatological liquid composition comprising an alkaline agent suitable for use in a skin care composition, and from about 0.1% to about 10% of at least one surfactant/emulsifying agent in a cosmetically acceptable vehicle, wherein the pH of the second dermatological liquid composition ranges from greater than about 7 to about 12;
 d) allowing the second dermatological liquid composition to dry; and
 e) applying a moisturizer, sunscreen and/or makeup to the skin when the first and second dermatological liquid compositions remain on the skin;

the first dermatological liquid composition comprising:

|  | weight percent | |
| --- | --- | --- |
| ingredient | from | to |
| chelating agent | 0.01% | 0.3% |
| witch hazel distillate | 0.01% | 20.0% |
| surfactant/emulsifying agent | 0.01% | 25.0% |
| salicylic acid | 0.1% | 5.0% |
| lactic acid | 0.1% | 20.0% |
| glycolic acid | 0.1% | 20.0% |
| ammonia, dissolved | 0.0% | 35.0% |
| preservative | 0.01% | 2.0% |
| acetone | 0.0% | 10.0% |
| alcohol | 1.0% | 50.0% |
| purified water | balance to 100%; and | | the second dermatological liquid composition comprising:

|  | weight percent | |
| --- | --- | --- |
| ingredient | from | to |
| sodium bicarbonate | 0.1% | 15.0% |
| silicone | 0.0% | 50.0% |
| green tea extract | 0.0% | 75.0% |
| phospholipids | 0.0% | 10.0% |
| vitamin E | 0.0% | 10.0% |
| vitamin A | 0.0% | 10.0% |
| ascorbyl palmitate | 0.0% | 10.0% |
| preservative | 0.0% | 6.0% |
| chelating agent | 0.0% | 2.0% |
| surfactant/emulsifying agent | 0.1% | 10.0% |
| water | balance to 100%. | |

50. The method of claim 49 wherein the first dermatological liquid composition and the second dermatological liquid composition are applied to a face.

51. The method of claim 49 wherein the first dermatological liquid composition is allowed to dry on the skin for about 3 minutes.

52. The method of claim 49, wherein the acid in the first dermatological liquid composition is selected from malic acid and citric acid.

53. A method for treating skin, comprising the sequential steps of:
 a) applying to the skin a first dermatological liquid composition comprising an effective amount of a skin renewal stimulating acid and a cosmetically acceptable vehicle, wherein the pH of the first dermatological liquid composition is between about 2.5 and about 4;
 b) neutralizing the first dermatological liquid composition by applying to the skin a second dermatological liquid composition comprising an alkaline agent suitable for use in a skin care composition, about 0.1% to about 10% of at least one surfactant/emulsifying agent and a cosmetically acceptable vehicle, wherein the pH of the second dermatological liquid composition ranges from greater than about 7 to about 12; and
 c) applying to the skin a moisturizer, sun screen and/or makeup without preceded by rinsing off the first and second dermatological liquid compositions from the skin.

\* \* \* \* \*